United States Patent
Katsuki

(10) Patent No.: US 10,451,577 B2
(45) Date of Patent: Oct. 22, 2019

(54) SUBSTANCE MEASURING METHOD AND MEASURING APPARATUS USING ELECTROCHEMICAL BIOSENSOR

(71) Applicant: ARKRAY, Inc., Kyoto (JP)

(72) Inventor: Koji Katsuki, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 365 days.

(21) Appl. No.: 15/458,902

(22) Filed: Mar. 14, 2017

(65) Prior Publication Data

US 2017/0269022 A1 Sep. 21, 2017

(30) Foreign Application Priority Data

Mar. 16, 2016 (JP) ................................. 2016-053071

(51) Int. Cl.
*G01N 27/327* (2006.01)

(52) U.S. Cl.
CPC ..... *G01N 27/3273* (2013.01); *G01N 27/3274* (2013.01)

(58) Field of Classification Search
CPC ...... G01N 27/327–3274; A61B 5/1486; A61B 5/14865
See application file for complete search history.

(56) References Cited

U.S. PATENT DOCUMENTS

| | | | |
|---|---|---|---|
| 5,108,564 A | 4/1992 | Szuminsky et al. | |
| 5,128,015 A | 7/1992 | Szuminsky et al. | |
| 5,298,144 A * | 3/1994 | Spokane | C12Q 1/002 204/403.1 |
| RE36,268 E | 8/1999 | Szuminsky et al. | |
| 7,045,054 B1 * | 5/2006 | Buck | A61B 5/14532 204/403.1 |
| 2015/0129425 A1 * | 5/2015 | Tsukada | C12Q 1/006 204/403.14 |
| 2016/0177365 A1 | 6/2016 | Katsuki | |

FOREIGN PATENT DOCUMENTS

| | | | | |
|---|---|---|---|---|
| EP | 3032250 A1 * | 6/2016 | ........... | G01N 27/416 |
| WO | 2014/140172 A1 | 9/2014 | | |

OTHER PUBLICATIONS

Claussen et al., "Electrochemical Glucose Biosensor of Platinum Nanospheres Connected by Carbon Nanotubes," Journal of Diabetes Science and Technology vol. 4, issue 2, Mar. 2000 (Year: 2000).*
Extended European Search Report issued in corresponding European Patent Application No. 17161299.7 dated Jul. 14, 2017.

* cited by examiner

*Primary Examiner* — Alexander S Noguerola
(74) *Attorney, Agent, or Firm* — Morgan, Lewis & Bockius LLP

(57) ABSTRACT

Provided is a measuring method using a biosensor, the method including: introducing a sample containing a substance to be measured into an electrochemical measurement cell, wherein the electrochemical measurement cell comprises: an insulating base plate; and an electrode system applying a first voltage to the electrode system; applying a second voltage to the electrode system; obtaining a first signal; obtaining a second signal; and correcting the second signal by the first signal, to determine the concentration of the substance to be measured in the sample.

17 Claims, 5 Drawing Sheets

(A)

(B)

SUBSTANCE MEASURING METHOD AND MEASURING APPARATUS USING ELECTROCHEMICAL BIOSENSOR

TECHNICAL FIELD

The present invention relates to a measuring method and a measuring apparatus using an electrochemical biosensor which utilizes an enzyme reaction, for analyzing a substance to be measured contained in a biogenic substance or the like.

BACKGROUND ART

Patent Document 1 discloses a method for measuring the concentration of a substance using an electrochemical biosensor, in which an electrode containing an oxidoreductase, an oxidizing agent, and a buffer is used. In the measurement method, after allowing an enzyme reaction to substantially complete, a potential is applied between the electrode and a sample to measure a Cottrell current, and the concentration of the substance is measured based on the thus measured Cottrell current. Since the Cottrell current is affected by the diffusion of the substance, Patent Document 1 discloses the measurement of a diffusion controlled current, in terms of reaction kinetics. On the other hand, Patent Document 2 discloses a method in which the concentration of a substance is measured by detecting a current resulting from the charge transfer process, not the diffusion process of the substance, and measuring the concentration of the substance based on the detected current. Since this method allows for measuring the concentration of a substance without being affected by the diffusion, it is possible to carry out the measurement with a lower cost and shorter time, as compared to the method disclosed in Patent Document 1.

PRIOR ART DOCUMENTS

Patent Documents

Patent Document 1: JP 2901678 B
Patent Document 2: WO 2015/020149

SUMMARY OF THE INVENTION

As described above, the method disclosed in Patent Document 2 measures a charge transfer limiting current, not a current dependent on the diffusion of a substance. Since the value of the measured current is affected by an enzyme activity and the amount of enzyme, the variation in the measured values obtained by a plurality of sensors has been a problem.

Accordingly, an object of the present invention is to provide a method and an apparatus for measuring a substance using an electrochemical biosensor, in which the variation in the measured values obtained by a plurality of sensors due to the enzyme activity and the amount of enzyme is reduced, and in which the measurement can be carried out with a higher accuracy, and using a simple system.

The present inventors have found out, as a result of intensive studies, that the above mentioned problems can be solved by performing a self-calibration of a sensor. For example, in the self-calibration of a sensor, a first potential and a second potential are applied to the electrodes; the concentration of a substance in a sample is measured; and further, a signal reflecting the amount or the activity of an oxidoreductase which is capable of catalyzing an oxidation reduction reaction and contributing to an electron transfer to and from the electrode is actually measured in the sensor; and the measurement result of the concentration of the substance in the sample is corrected by the above obtained signal reflecting the amount or the activity of the oxidoreductase. By carrying out the self-calibration, it is possible to reduce the variation in the measured values obtained by a plurality of sensors, and to measure the concentration of the substance accurately. The present invention has thus been completed.

The method according to the present invention comprises:
a step of introducing a sample containing a substance to be measured into an electrochemical measurement cell,
wherein the electrochemical measurement cell comprises:
an insulating base plate; and an electrode system formed on the insulating base plate and comprising two or more electrodes, wherein at least one of the electrodes contains an oxidoreductase;
a first voltage application step of applying a first voltage to the electrode system;
a second voltage application step of applying a second voltage to the electrode system;
a step of obtaining a first signal dependent on the amount of the oxidoreductase which is capable of catalyzing an oxidation reduction reaction and contributing to an electron transfer to and from the electrode, in the first voltage application step;
a step of obtaining a second signal dependent on the amount of the substance to be measured in the sample, in the second voltage application step; and
a step of correcting the second signal by the first signal, to determine the concentration of the substance to be measured in the sample.

In the above mentioned method, in some embodiments, the first voltage may be a voltage of not more than the reduction potential of the oxidoreductase, and the second voltage be a voltage of not less than the oxidation potential of the oxidoreductase.

Further, the above mentioned method in accordance with some embodiments comprises:
calculating a correction coefficient from the degree of deviation of the measured value of the first signal from a calibration curve representing the relationship between the value of the first signal and the value of the second signal;
correcting the measured value of the second signal with the correction coefficient; and
determining the concentration of the substance based on the corrected value of the second signal.

In the above mentioned method, the second signal in some embodiments may be a charge transfer limiting current. The charge transfer limiting current in some embodiments may be a steady-state current observed after the generation of a transient current due to the charging of an electric double layer, and in additional embodiments may be a current represented by the Equation (2) shown below.

Further, the oxidoreductase in some embodiments contains pyrroloquinoline quinone or flavin adenine dinucleotide, or has a subunit or a domain containing heme.

For example, the oxidoreductase in some embodiments may be an enzyme having a glucose oxidation activity, such as glucose dehydrogenase, and the substance to be measured may be glucose, for example.

The apparatus according to the present invention comprises:
a biosensor comprising:
an electrochemical measurement cell comprising:
an insulating base plate; and an electrode system formed on the insulating base plate, and comprising two or more electrodes, wherein at least one of the electrodes contains an oxidoreductase;

a control section configured to control the application of a first voltage and a second voltage to the biosensor;

a detection section configured to detect a first signal and a second signal obtained by the application of the first voltage and the second voltage to the biosensor;

an arithmetic section configured to correct the second signal by the first signal, to determine the concentration of a substance contained in a sample; and an output section configured to output the calculated concentration of the substance.

In the above mentioned measuring apparatus, the substance to be measured in some embodiments may be glucose, and the oxidoreductase in some embodiments may be an enzyme having a glucose oxidation activity, such as glucose dehydrogenase.

According to the present invention, it is possible to reduce the influence of the enzyme activity and the amount of enzyme, and to reduce the variation in the measured values obtained by a plurality of sensors, in the measurement of a substance using an electrochemical biosensor. Conventionally, the calibration of a biosensor has generally been carried out for each production lot of the sensors. However, the present invention allows for performing the calibration for each individual sensor, thereby enabling to further improve the measurement accuracy of the sensor.

EMBODIMENTS FOR CARRYING OUT THE INVENTION

Figure 1:
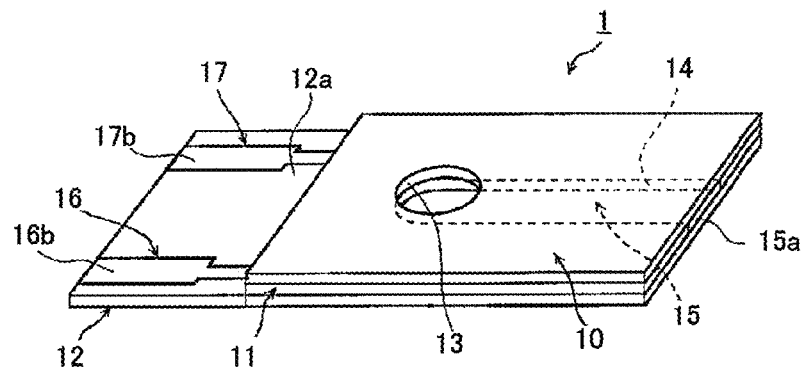
FIG. 1 is a diagram illustrating one embodiment of the structure of a biosensor according to the present invention. Item A of FIG. 1 is an overall perspective view, and item B of FIG. 1 is an exploded perspective view, of the biosensor.
Figure 1:
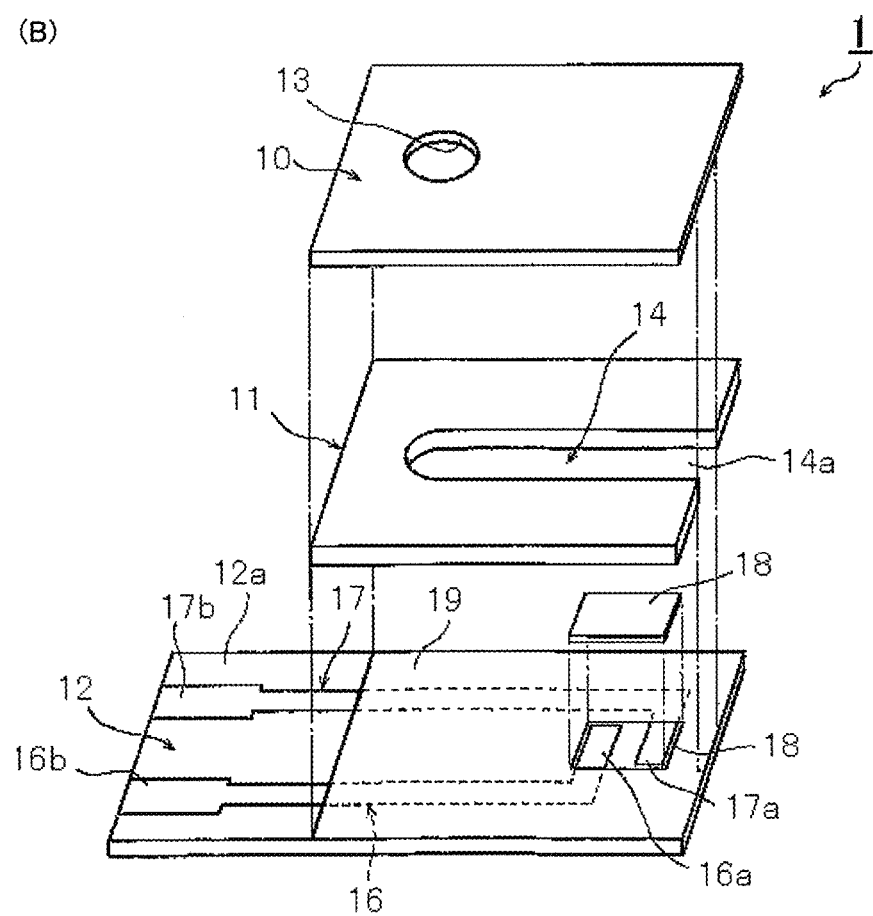

Embodiments of the present invention will now be described. However, the embodiments to be described below are provided for illustrative purposes, and the present invention is not limited to the constitution of the following embodiments.

The method of measuring a substance using a biosensor according to the present invention comprises:

a step of introducing a sample containing a substance to be measured into an electrochemical measurement cell,
wherein the electrochemical measurement cell comprises:
an insulating base plate; and an electrode system formed on the insulating base plate and comprising two or more electrodes, wherein at least one of the electrodes contains an oxidoreductase;

a first voltage application step of applying a first voltage to the electrode system;

a second voltage application step of applying a second voltage to the electrode system;

a step of obtaining a first signal dependent on the amount of the oxidoreductase which is capable of catalyzing an oxidation reduction reaction and contributing to an electron transfer to and from the electrode, in the first voltage application step;

a step of obtaining a second signal dependent on the amount of the substance to be measured in the sample, in the second voltage application step; and a step of correcting the second signal by the first signal, to determine the concentration of the substance to be measured in the sample.

The substance to be measured is not particularly limited as long as it can be measured by the measurement method using a biosensor according to the present invention. However, the substance to be measured in some embodiments may be a substance derived from a living body, which can serve as an index of a disease and/or health condition, and examples thereof include glucose, cholesterol, lactic acid and the like.

The sample is not particularly limited as long as it contains the substance to be measured. In some embodiments, a biological sample may be blood or urine.

The components of the electrochemical measurement cell included in the electrochemical biosensor which can be used in the measurement method according to the present invention will be described below.

<Working Electrode>

The working electrode can be obtained, for example, by disposing an electrode material on an insulating base plate to form an electrode, and by disposing a reagent layer containing at least an oxidoreductase in the vicinity of the thus formed electrode.

The electrode is formed, for example, using a carbon material such as carbon. Alternatively, a metallic material such as gold (Au), platinum (Pt), silver (Ag), palladium (Pd), or ruthenium (Ru) can also be used.

The insulating base plate is made, for example, of an insulating material, and examples thereof include various types of resins (plastics), such as thermoplastic resins, for example, polyetherimide (PEI), polyethylene terephthalate (PET) and polyethylene (PE), polyimide resins, and epoxy resins; glasses; ceramics; papers; and the like.

The size and the thickness of the electrode and the insulating base plate can be determined as appropriate.

<Oxidoreductase>

The oxidoreductase can be any enzyme capable of oxidizing and reducing the substance to be measured, and can contain at least one of pyrroloquinoline quinone (PQQ) and flavin adenine dinucleotide (FAD), as a catalytic subunit and a catalytic domain. Examples of the oxidoreductase containing PQQ include PQQ glucose dehydrogenase (PQQGDH). Examples of the oxidoreductase containing FAD include cytochrome glucose dehydrogenase (CyGDH) and glucose oxidase (GOD), having an α subunit containing FAD.

In addition, the oxidoreductase can contain an electron transfer subunit or an electron transfer domain. Examples of the electron transfer subunit include a subunit containing heme which has a function of giving and receiving electrons. Examples of the oxidoreductase having the subunit containing heme include those containing cytochrome. For example, a fusion protein of glucose dehydrogenase or PQQGDH with cytochrome can be used.

Further, examples of the enzyme containing the electron transfer domain include cholesterol oxidase and quinoheme ethanol dehydrogenase (QHEDH (PQQ Ethanol dh). As the electron transfer domain, a domain containing cytochrome containing heme which has a function of giving and receiving electrons may be used. Examples thereof include "QHGDH" (fusion enzyme; GDH with heme domain of QHGDH)), sorbitol dehydrogenase (Sorbitol DH), D-fructose dehydrogenase (Fructose DH), Glucose-3-Dehydrogenase derived from *Agrobacterium tumefasience* (G3DH from *Agrobacterium tumefasience*), cellobiose dehydrogenase, and lactate dehydrogenase. The fusion protein of PQQGDH with cytochrome, which is an example of the above mentioned subunit containing cytochrome, and a cytochrome domain of PQQGDH, which is an example of the domain containing cytochrome, are disclosed, for example, in International Publication No. WO 2005/030807.

Further, in one aspect, the oxidoreductase may be an oligomeric enzyme comprising at least a catalytic subunit and a subunit containing cytochrome containing heme which has a function as an electron acceptor.

The substance to be measured can be any substance which serves as a substrate for the oxidoreductase. For example, since cellobiose dehydrogenase oxidizes not only cellobiose but also glucose, glucose can also be used as the substance to be measured.

In order to measure a charge transfer limiting current to be described later, in some embodiments, a "direct electron transfer-type (enzyme) electrode" may be used as the working electrode. The "direct electron transfer-type (enzyme) electrode" as used herein refers to a type of an enzyme electrode in which electrons are transferred between the enzyme and the electrode in such a way that electrons generated by an enzymatic reaction in a reagent layer are directly transferred to the electrode without the involvement of an oxidation-reduction substance, such as an electron transfer mediator.

It should be noted that the limit distance within which the direct electron transfer could occur in a physiological reaction system is said to be from 1 to 2 nm. Therefore, it is important that the molecules of the enzyme be positioned such that the transfer of electrons from the enzyme to the electrode is not interfered.

In order to measure the charge transfer limiting current, it is important that the molecules of an oxidoreductase be positioned in the vicinity of the electrode. Examples of the method therefor include: a method in which the molecules of an oxidoreductase are chemically immobilized to the electrode; a method in which the molecules of an oxidoreductase are indirectly immobilized to the electrode using a binder or the like, and a method in which the molecules of an oxidoreductase are allowed to be physically adsorbed on the electrode; but not limited thereto.

The enzyme reagent layer on the working electrode can contain electrically conductive particles. By containing electrically conductive particles, it can be expected that electrons are suitably transferred to and from the electrode. For example, particles of a metal such as gold, platinum, silver or palladium; or a higher-order structure made of a carbon material can be used, as the electrically conductive particles. The higher-order structure can contain, for example, carbon particles or carbon fine particles, such as particles of electrically conductive carbon black, carbon nanotube (CNT) or fullerene. Examples of electrically conductive carbon black include Ketjen Black (manufactured by Degussa Corporation), BLACK PEARLS (manufactured by Cabot Corporation) and the like.

The enzyme reagent layer on the working electrode can also contain an electrically conductive polymer. The electrically conductive polymer in some embodiments may be a water-soluble polymer, and examples thereof include polyaniline, polyethylenedioxythiophene and the like. Representative examples thereof include an aqueous solution of sulfonated polyaniline (trade name: aquaPASS), manufactured by Mitsubishi Rayon Co., Ltd.

The enzyme reagent layer on the working electrode can also contain a binder. The binder in some embodiments may be a water soluble binder, and specific examples thereof include an oxazoline group-containing water soluble polymer and the like.

The above mentioned working electrode is prepared, for example, as follows. A carbon layer which functions as an electrode is formed on one surface of an insulating base plate. For example, a carbon film having a desired thickness (for example, about 10 μm) can be prepared by screen-printing a carbon ink on one surface of the insulating base plate in the form of a film having a predetermined thickness (for example, about 100 μm). Instead of the carbon layer, it is also possible to form a metal layer having a desired thickness (for example, about 30 nm) by depositing a metallic material by physical vapor deposition (PVD, for example by sputtering), or by chemical vapor deposition (CVD).

Next, an enzyme reagent layer is formed on the electrode. First, a solution containing an oxidoreductase, and electrically conductive particles and/or an electrically conductive polymer is prepared, and the resulting solution is dropped on the surface of the electrode. Then, the solution is allowed to be dried and solidified on the electrode, to obtain a working electrode on top of which an enzyme reagent layer is formed.

The electrode system included in the biosensor to be used in the present invention may include a counter electrode, in addition to the above described working electrode. As a counter electrode, it is possible to use any electrode which can be generally used as the counter electrode in a biosensor. Examples thereof include: a carbon electrode prepared in the form of a film by screen-printing; a metal electrode prepared in the form of a film by physical vapor deposition (PVD, for example, sputtering) or chemical vapor deposition (CVD); and a silver/silver chloride electrode prepared in the form of a film by screen-printing. Further, the electrode system of the biosensor to be used in the present invention may be a 3-electrode system, in which a silver/silver chloride electrode is used as a reference electrode.

(Method for Measuring the Concentration of Substance to be Measured in Sample)

In the method for measuring a substance using a biosensor according to the present invention, a sample containing a substance is introduced into the electrochemical measurement cell, and then the first and the second voltages are applied to the electrode system, to obtain the first and the second signals.

In the above described method, the first voltage in some embodiments may be a voltage of not more than the reduction potential of the oxidoreductase which is used in the working electrode. By applying a voltage of not more than the reduction potential of the oxidoreductase, it is possible to obtain the first signal, which does not depend on the concentration of the substance in the sample, but depends on the amount of the oxidoreductase which is capable of catalyzing an oxidation reduction reaction and contributing to the electron transfer to and from the electrode, namely, the value of a first current (reduction current value).

On the other hand, the second voltage in some embodiments may be a voltage of not less than the oxidation potential of the oxidoreductase, which is used in the working electrode. By applying a voltage of not less than the oxidation potential of the oxidoreductase, it is possible to obtain the second signal, which depends on the concentration of the substance in the sample, namely, the value of a second current (oxidation current value).

The oxidation potential and the reduction potential of the enzyme to be used can be obtained by a known method. A known analysis method such as a cyclic voltammetry can be used, for example, to confirm the reduction potential of the electron transfer site of the enzyme.

For example, when the oxidoreductase is CyGDH, the first voltage may be from −0.01 to −0.4 V, or from −0.1 to −0.2 V; and the second voltage may be from 0.01 to 0.8 V, or from 0.05 to 0.4 V. In some embodiments, the first voltage may be from −0.01, −0.03, −0.05, −0.08 or −0.10 V to −0.20, −0.25, −0.30, −0.35, or −0.4 V. In additional embodiments, the second voltage may be from 0.01, 0.02, 0.03, 0.04, or 0.05 V to 0.4, 0.5, 0.6, 0.7 or 0.8 V.

The type of the second signal, which depends on the concentration of the substance in the sample, is not particularly limited. However, the second signal in some embodiments may be a charge transfer limiting current resulting from the transfer of electrons derived from the substance to be measured to the electrode. As used herein, the charge transfer limiting current resulting from the transfer of electrons derived from the substance to be measured to the electrode is a current which is generated when the electrons are transferred from the oxidoreductase to the electrode due to the reaction between the oxidoreductase and the substance to be measured. Further, the charge transfer limiting current is a steady-state current which does not depend on time, and in some embodiments may be a steady-state current observed after the generation of a transient current due to the charging of an electric double layer.

The charge transfer limiting current in some embodiments may be represented by the following Equation (1). It can be seen from the Equation (1) that the current is proportional to the concentration of the substrate and to the enzyme reaction rate constant, and when the constant term is defined as X, it can be expressed as Equation (2). Although not shown in Equations (1) and (2), the constant term X may include a correction coefficient and/or the like.

[Equation 1]

$$i = \frac{nFAC_s^0 K_{cat} \tau_E}{Km} \quad (1)$$

i: Current (A)
n: Reaction electron number (eq/mol)
F: Faraday constant (96,485 C/eq)
A: Electrode surface area (cm$^2$)
$C_s^O$: Concentration of substrate (S)(mol/cm$^3$)
$\tau_E$: Amount of Enzyme (mol)
Kcat/Km: enzyme reaction rate constant

[Equation 2]

$$i = X \cdot \frac{K_{cat}}{Km} \cdot C_s^0 \quad (2)$$

Further, it is possible to confirm whether the electrode system is charge transfer controlled, by examining the presence or absence of a peak, and the pattern of current increase due to the sweep direction of the voltage, using cyclic voltammetry or the like.

The application of the first voltage and the application of the second voltage to the working electrode may be carried out continuously, but, in some embodiments, may be carried out intermittently with a certain interval therebetween. For example, in an exemplary embodiment, the second voltage is applied after a period of from three to ten seconds after the application of the first voltage. There is no particular limitation on the manner in which a voltage is applied to the electrode. However, in order to efficiently measure the charge transfer limiting current, a stepwise application may be used.

The measurement of the first signal in some embodiments may be carried out after one to five seconds after the application of the first voltage, and the measurement of the second signal in some embodiments may be carried out three to 60 seconds after the application of the second voltage.

Note, however, that the application of the first voltage and the application of the second voltage to the working electrode, and the measurement of the first signal and the measurement of the second signal resulting therefrom, may be carried out entirely independently. For example, since the value of the first signal does not depend on the amount of the substance to be measured contained in the sample, as will be described below, the application of the first voltage and the measurement of the first signal may be carried out in advance in a state where the sample containing the substance to be measured is absent, and the application of the second voltage and the measurement of the second signal may be carried out later in a state where the sample containing the substance to be measured is present.

The value of the second signal depends on the amount of the substance to be measured in the sample, but it also depends on the amount of the oxidoreductase which is capable of catalyzing an oxidation reduction reaction and contributing to the electron transfer to and from the electrode. On the other hand, although the value of the first signal depends on the amount of the oxidoreductase, it does not depend on the amount of the substance to be measured in the sample. Accordingly, by correcting the value of the second signal with the value of the first signal, it is possible to measure the amount of the substance to be measured in the sample, without being affected by the activity and the amount of the oxidoreductase.

For example, the value of the current (the first signal: reduction current value) which is measured when a constant voltage of not more than the reduction potential of the oxidoreductase is applied to the electrode system, positively correlates (has a proportional relationship) with the amount of the oxidoreductase. Therefore, the relative amount of the enzyme (relative total activity) of the enzyme electrode used in the measurement can be determined in advance, from the reduction current value.

On the other hand, when a constant voltage of not less than the oxidation potential of the oxidoreductase is applied to the electrode system, a current proportional to the concentration of the substance to be measured flows, and from the value of the current (the second signal: oxidation current value), the value of the concentration (interim value) of the substance to be measured, such as glucose can be determined.

In the case of the charge transfer limiting current, the concentration (interim value) of the substance to be measured can be calculated from the measured value of the current, based on the above described Equation (1). It is also possible to prepare a calibration curve in advance, using a sample having a known concentration, and to calculate the concentration from the measured current value, based on the calibration curve. In addition, the concentration of the sample can also be calculated by multiplying a correction coefficient obtained by a test to Equation (1), and the like. In this case, the correction coefficient is included in the constant term X in Equation (2).

Further, if the relationship between the oxidation current value dependent on the concentration of the substance to be measured, and the reduction current value dependent on the amount of the enzyme, is obtained in advance, it is possible to accurately measure the concentration of the substance to be measured, such as glucose, by performing correction with the reduction current value. In this case, the concentration (interim value) of the substance to be measured may be obtained in advance from the oxidation current value, and then the interim value of the concentration may be corrected with the reduction current value to obtain the concentration (corrected value) of the substance to be measured. Alternatively, the oxidation current value may be corrected with the reduction current value first, and subsequently, the concentration (corrected value) of the substance to be measured may be obtained based on the oxidation current value (corrected value).

According to the measurement method of the present invention, the measurement can be carried out either continuously or intermittently. In cases where a plurality of measurements are carried out continuously, once the reduction current value is obtained, the measured values can be corrected continuously based on the thus obtained value, without obtaining the reduction current value at every measurement.

(Measuring Apparatus for Measuring Substance to be Measured in Sample)

Next, a measuring apparatus 2 according to the present invention will be described with reference to the drawings. Although a glucose measuring apparatus which includes a glucose sensor as the biosensor is illustrated in the following embodiment, the measuring apparatus according to the present invention is not limited to the embodiment.

The measuring apparatus according to the present invention includes:

the above mentioned biosensor;

a control section configured to control the application of a first voltage and a second voltage to the biosensor;

a detection section configured to detect a first signal and a second signal obtained by the application of the first voltage and the second voltage to the biosensor;

an arithmetic section configured to correct the value of the second signal based on the value of the first signal, to determine the concentration of a substance contained in a sample; and an output section configured to output the calculated concentration of the substance.

Figure 6:
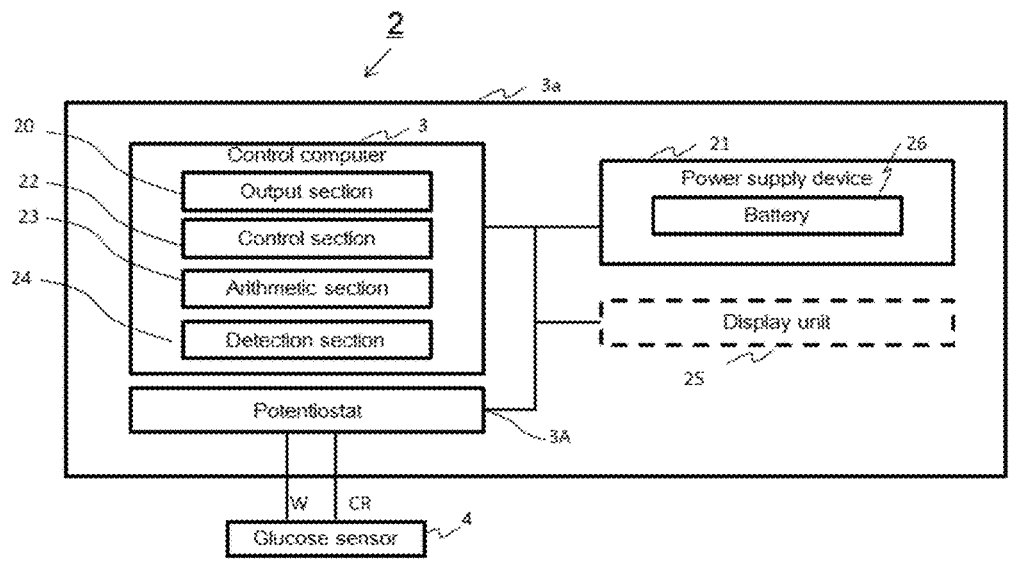
FIG. 6 is a schematic diagram illustrating one embodiment of a measuring apparatus according to the present invention.

FIG. 6 shows an example of the configuration of main electronic components included in the measuring apparatus 2. A control computer 3, a potentiostat 3A and a power supply device 21 are provided on a base plate 3a housed in a housing. The control computer 3 includes, as hardware, a processor such as CPU (central processing unit); a recording medium such as a memory (RAM (Random Access Memory) or ROM (Read Only Memory)); and a communication unit. When the processor loads a program stored in the recording medium (for example, the ROM) to the RAM, and executes the program, the control computer 3 functions as an apparatus comprising an output section 20, a control section 22, an arithmetic section 23 and a detection section 24. The control computer 3 may also include an auxiliary memory such as a semiconductor memory (EEPROM or flash memory) or a hard disk.

The control section 22 controls the timing for applying a voltage and the value of the voltage to be applied, and the like. The power supply device 21 includes a battery 26, and supplies electricity to the control computer 3 and the potentiostat 3A for operation. It is also possible to dispose the power supply device 21 outside the housing. The potentiostat 3A is a device which maintains the potential of the working electrode constant with respect to the potential of the reference electrode. The potentiostat 3A, which is controlled by the control section 22, applies predetermined amount of voltages (the first and the second voltages) between the counter electrode (reference electrode) and the working electrode of the glucose sensor (enzyme electrode) 4 using terminals CR and W; measures the response currents (the first and the second currents) of the working electrode which can be obtained at the terminal W; and send the results of the measurements to the detection section 24.

The arithmetic section 23 corrects the value of the second current detected at the glucose sensor with the value of the first current, calculates the concentration of glucose based on the corrected value of the second current, and stores the obtained value. Note, however, that the calculation for obtaining the glucose concentration (interim value) from the value of the second current may be carried out first, and then the calculated glucose concentration (interim value) may be corrected with the value of the first current. The output section 20 carries out data communication between the output section 20 and the display section unit 25, and sends the calculated result of the concentration of the substance to be measured provided by the arithmetic section 23 to the display section unit 25. The display section unit 25 is capable of displaying, for example, the calculated result of the glucose concentration which is received from the measuring apparatus 2, on a display screen in a predetermined format.

Figure 7:
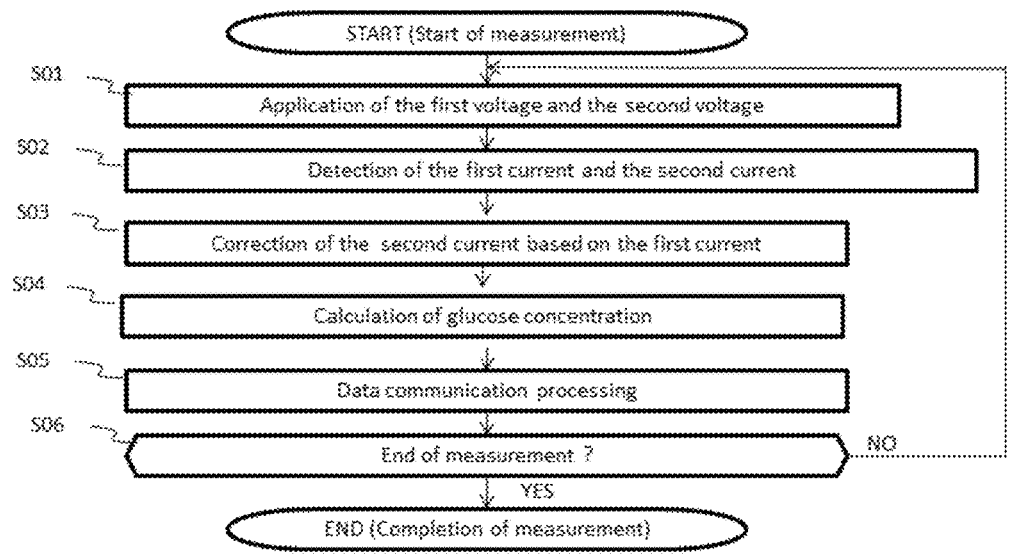
FIG. 7 is a flow chart illustrating one embodiment of a measurement program using the measuring apparatus according to the present invention.

FIG. 7 is a flow chart showing an example of the processing sequence of the glucose concentration measurement carried out by the control computer 3. When the CPU (control section 22) of the control computer 3 receives an instruction to start the measurement of the glucose concentration, the control section 22 controls the potentiostat 3A to apply the predetermined amount of voltages (the first and the second voltages) to the glucose sensor, and starts measuring the respective response currents (the first and the second currents) (Step S01). The detection of the installation of a sensor to the measuring apparatus may be used as the instruction to start the measurement of the concentration.

Next, the potentiostat 3A measures the response currents, namely, the first and the second currents, obtained by the application of voltages, and sends the measured current values to the detection section 24 (Step S02).

The arithmetic section 23 firstly carries out a correction of the value of the second current with the value of the first current (Step S03). For example, the calculation formulae or the data of the calibration curve representing the relationship between the value of the second current and the value of the first current are preinstalled to the arithmetic section 23 in the control computer 3, and the arithmetic section 23 corrects the value of the second current using these calculation formulae or the calibration curve. In one aspect, the calculation formulae or the data of the calibration curve representing the relationship between the value of the second current and the value of the first current may be prepared for each of the respective concentration levels of glucose. For example, the calculation formulae or the data of the calibration curve are prepared for each of the respective glucose concentration levels of 0, 100, 200, 300, 400, 500, 600, 700, 800, 900, and 1000 mg/dL. Of these, the calibration curve closest to the value of the second current is selected, and based on the selected calibration curve, the deviation between the theoretical value and the measured value, of the value of the first current with respect to the value of the second current, is evaluated. Then a correction coefficient is calculated based on the degree of the deviation, and the value of the second current is corrected based on the degree of the deviation. The glucose concentration levels for each of which the calculation formulae or the data of the calibration curve representing the relationship between the value of the second current and the value of the first current are prepared, are not limited to the above mentioned concentration levels, and the concentration levels may be set arbitrarily, for example, at every 5 mg/dL, or every 10 mg/dL.

Further, the arithmetic section 23 calculates the glucose concentration based on the corrected value of the second current (Step S04). For example, the formulae for calculating the glucose concentration or the data of the calibration curve of the glucose concentration are preinstalled to the arithmetic section 23 in the control computer 3, and the arithmetic section 23 calculates the glucose concentration utilizing these calculation formulae or the calibration curve.

It is also possible to carry out Step S04 before carrying out Step S03. For example, the calculation for obtaining the glucose concentration (interim value) from the value of the second current may be carried out first, and then the calculated glucose concentration (interim value) may be corrected with the value of the first current.

The output section 20 sends the calculated result of the corrected glucose concentration to the display section unit 25, through a communication link provided between the output section 20 and the display section unit 25 (Step S05). Thereafter, the control section 22 determines if there are any measurement errors detected (Step S06); completes the measurement if there is no error; and displays the glucose concentration on the display section. If there are some errors, a notification of error is displayed, and then the flow sequence shown in FIG. 7 is completed.

EXAMPLES

The present invention is not limited to the embodiments of the following Examples.

Examples of the biosensor is described below for a glucose sensor.
<Production Method of Glucose Sensor>
FIG. 1 shows an example of the glucose sensor.
As shown in FIG. 1, the glucose sensor 1 includes a cover plate 10, a spacer 11, and a base plate 12.

The cover plate 10 is provided with a hole 13, and the spacer 11 is provided with a slit 14 having a narrow width, which communicates with the hole 13 and opens at a distal end opening 14a. In the state where the cover plate 10 and the spacer 11 are laminated on an upper surface 12a of the base plate 12, such that the spacer 11 is sandwiched between the base plate 12 and the cover plate 10, the slit 14 defines a capillary 15. The capillary 15 communicates with the exterior of the glucose sensor through the distal end opening 14a of the slit 14 and the hole 13. The distal end opening 14a defines a sample liquid introduction port 15a, and a sample liquid supplied through the sample liquid introduction port 15a moves within the capillary 15 toward the hole 13 due to the capillary phenomenon.

A first electrode 16, a second electrode 17, and a reagent layer 18 are provided on the upper surface 12a of the base plate 12.

Overall, the first and the second electrodes 16 and 17 extend in the longitudinal direction of the base plate 12, and end portions 16a and 17a of the electrodes extend in the width direction of the base plate 12. The upper surface 12a of the base plate 12 is covered by an insulating film 19 such that the end portions 16a, 16b, 17a, and 17b of the first and the second electrodes 16 and 17 are exposed.

The reagent layer 18 is disposed so as to bridge between the end portions 16a and 17a of the first and the second electrodes 16 and 17. The reagent layer 18 contains glucose dehydrogenase.

In some embodiments, the glucose sensor is produced according to the following method.
<Base Electrode>

As the base electrode material, an electrically conductive carbon ink (FTU series; manufactured by Asahi Chemical Research Laboratory Co., Ltd.) was used, and this ink was pattern-printed on one surface of a polyethylene terephthalate base material (E-22; manufactured by Toray Industries, Inc.) (length: 50 mm, width: 5 mm, thickness: 250 pin) to form a 2-electrode pattern. Further, a silver/silver chloride ink (manufactured by BAS Inc.) was coated on one of the electrodes, and dried at 80 C° for 20 minutes, to form a silver/silver chloride electrode to be used as a counter electrode.

Next, an insulation resin polyester ink (UVF series; manufactured by Asahi Chemical Research Laboratory Co., Ltd.) was printed on the electrodes by screen printing. Each of the surface area of the electrodes defined by the electrode pattern and insulation pattern was set to be 0.5 mm$^2$.
<Formation of Enzyme Reagent Layer>

An enzyme reagent containing cytochrome-containing glucose dehydrogenase (CyGDH), electrically conductive particles (carbon black: Ketjen Black KJB), an electrically conductive polymer (polyaniline) as a conductive auxiliary agent, and a binder (oxazoline group-containing water soluble polymer) was prepared, and 0.04 μL of the resulting solution was dropped on the electrodes and dried at 100 C° for 30 minutes to prepare an enzyme reagent layer. The final concentration of the enzyme reagent is as follows.
<Composition of the Enzyme Reagent>
KJB: 0.4 wt %
Enzyme (CyGDH): 7 mg/mL
Sodium phosphate buffer solution: 10 mM, pH 7

Binder (oxazoline group-containing water soluble polymer, EPOCROS WS-700; manufactured by NIPPON SHOKUBAI Co., Ltd.): 5.0% (w/v)

Polyaniline (aquaPASS; manufactured by Mitsubishi Rayon Co., Ltd.): 0.2% (w/v)

<Formation of Capillary>

The capillary was formed in the following manner. On the base electrode on the surface of which the enzyme reagent layer had been formed, a double-sided adhesive tape and a hydrophilic film were pasted to form a capillary, thereby forming the sensor.

<Measurement of Glucose>

The glucose concentration was measured in the following manner.

(1) Measurement of Amount of Enzyme (Self-Calibration Measurement)

A step voltage of from −0.14 V to −0.2 V was applied to the electrode system for five seconds, to detect the reduction current. The current value four seconds after the application of the voltage was sampled, and defined as the reduction current value of the enzyme.

(2) Measurement of Glucose

After the completion of (1), an open circuit period of five seconds was inserted, and then a voltage of 0.07 V was applied to the electrode system for 15 seconds, to detect the oxidation current dependent on the glucose concentration. The current value measured ten seconds after the application of the voltage was defined as the oxidation current value for determining the glucose concentration.

<Results>

Figure 2:
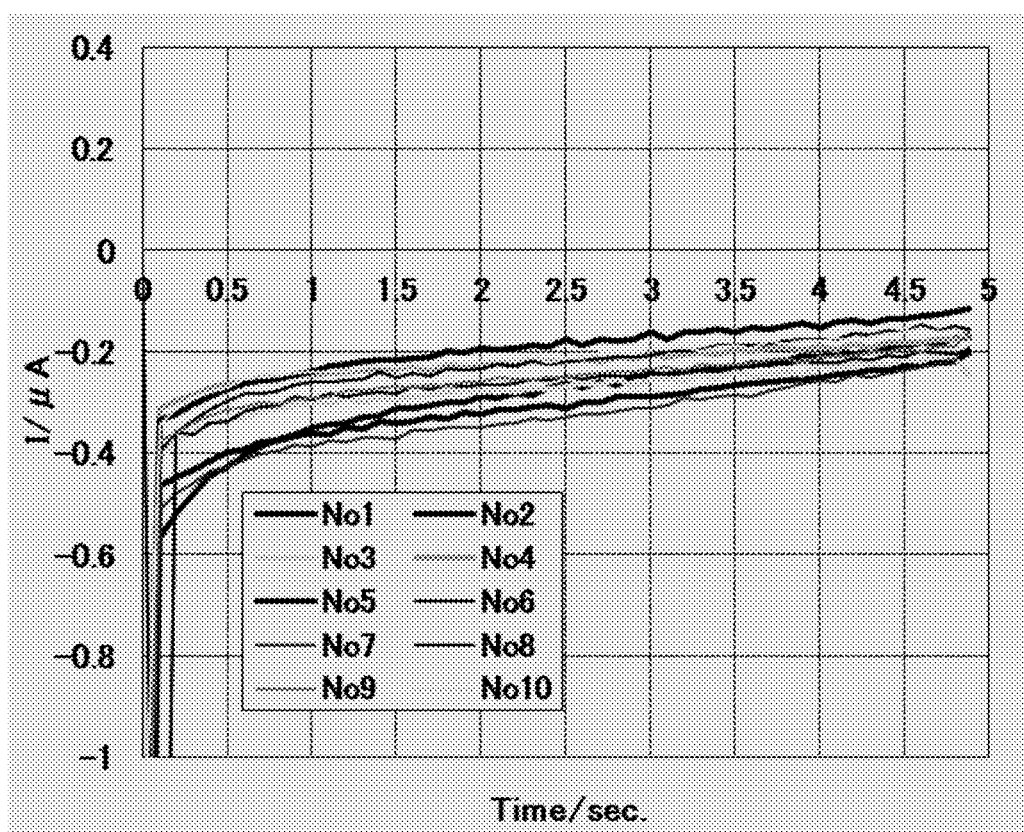
FIG. 2 is a diagram illustrating the results of the measurements of reduction current, carried out by applying a reduction potential to a plurality of sensors. A whole blood sample containing 600 mg/dL of glucose was used.
Figure 3:
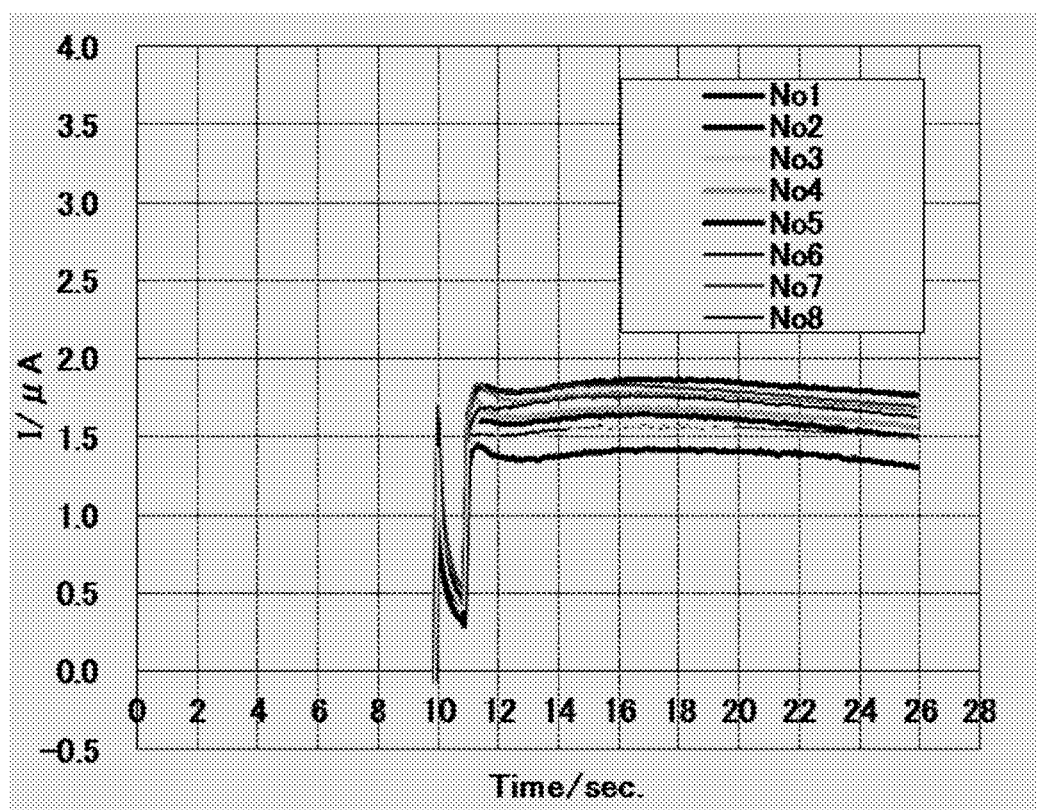
FIG. 3 is a graph illustrating the results of chronoamperometry measurements, carried out by applying an oxidation potential to a plurality of sensors. A whole blood sample containing 600 mg/dL of glucose was used.

A whole blood sample containing 600 mg/dL of glucose was introduced to the sensors of a plurality of production lots. Subsequently, the reduction potential, and then the oxidation potential were applied according to the above described (1) and (2), to measure the reduction current and oxidation current. The results are shown in FIG. 2 and FIG. 3. FIG. 3 shows a graph in which the results of the self-calibration measurement carried out in (1) are omitted. It can be seen from FIG. 2 and FIG. 3 that the values of the reduction current and the oxidation current vary depending on the respective sensors.

Figure 4:
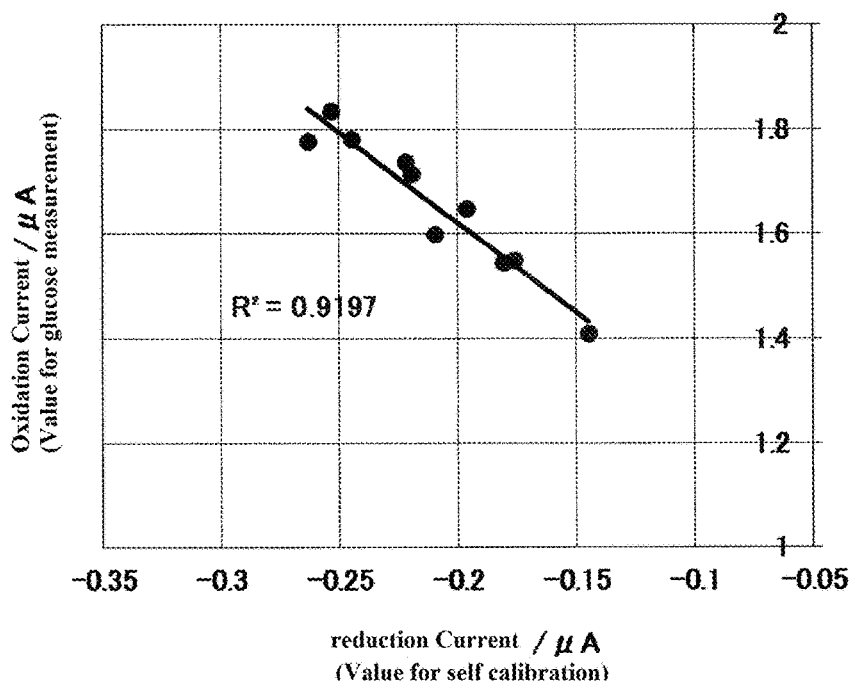
FIG. 4 is a graph obtained by plotting the measured values of the reduction current and the measured values of the oxidation current, when the measurement was performed using a whole blood sample containing 600 mg/dL of glucose, for each of the sensors.

The measured values of the reduction current and the oxidation current of the respective sensors were plotted to obtain the graph shown in FIG. 4. As can be seen from FIG. 4, the values of the oxidation current (measured ten seconds after voltage application) dependent on the concentration of the substance in the sample correlate with the values of the reduction current dependent on the enzyme activity and the amount of the enzyme in the sensor. Thus, it was considered possible that the variation in the measured values obtained by a plurality of sensors may be reduced by correcting the measured values of the oxidation current with the measured values of the reduction current.

Therefore, the measurement of the reduction current and the oxidation current was carried out using a whole blood sample containing a 134 mg/dL or 600 mg/dL of glucose, and the glucose concentration was calculated based on the measured results. The procedure for carrying out the correction is as follows. The calibration curve representing the correlation between the reduction current values and the oxidation current values was prepared for each of the samples having a glucose concentration of 134 mg/dL and 600 mg/dL.

(3) Correction of Measured Value of Glucose with Relative Amount of Enzyme (3-1) The reduction current values and the oxidation current values measured for the respective sensors are plotted, to obtain a calibration curve representing the correlation between the reduction current values and the oxidation current values (for example, FIG. 4).

(3-2) Using the calibration curve representing the correlation between the reduction current values and the oxidation current values, which has been prepared in advance as described in (3-1), the degree of deviation of the measured value of the reduction current from the calibration curve is determined, and a correction coefficient is calculated from the degree of deviation.

(3-3) The measured value of the oxidation current is multiplied by the correction coefficient calculated in (3-2), to obtain the oxidation current value (corrected value) for determining the glucose concentration, and the glucose concentration (corrected value) is calculated based on the corrected oxidation current value.

Figure 5:
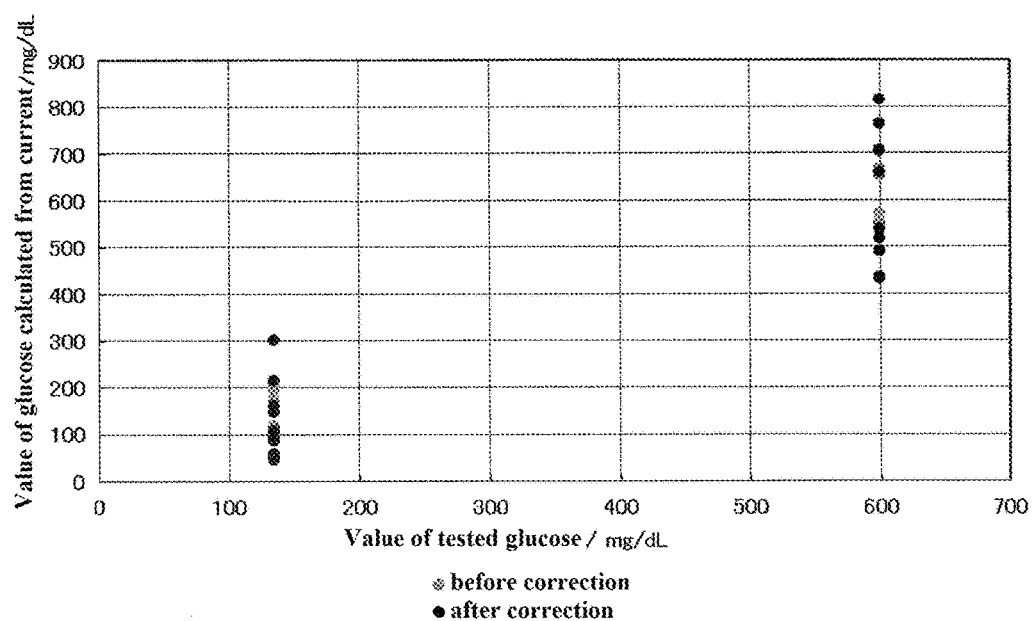
FIG. 5 is a graph obtained by plotting the measured values of the glucose concentration before and after the correction, when the measurement was performed using a whole blood sample containing 134 mg/dL or 600 mg/dL glucose, for each of the sensors.

The measured values of the glucose concentration before and after the correction were plotted to confirm the effect of correction in the measured values of glucose obtained by the self-calibration measurement. As a result, as shown in FIG. 5 and Table 1, it has been confirmed that the reproducibility is improved as compared to the data obtained without the correction (self-calibration), and that a high correction effect is obtained.

TABLE 1

| | C. V (%) | | | |
|---|---|---|---|---|
| | Current value | | Value of concentration calculated from current | |
| | Before correction | After correction | Before correction | After correction |
| 134 mg/dL | 8.8 | 6.6 | 33.2 | 25.1 |
| 600 mg/dL | 8.1 | 2.2 | 14.1 | 3.9 |

Based on the above, it has been found that it is possible to perform a self-calibration, namely, to calculate a correction coefficient derived from the amount of enzyme (enzyme activity) which is capable of catalyzing an oxidation reduction reaction and contributing to the electron transfer to and from the electrode, by detecting the reduction current of the electron transfer site of the enzyme, and to correct the measured result of the substance to be measured based on the correction coefficient. In other words, by measuring a reduction reaction derived from heme in the β subunit, which is the electron transfer site of the oxidoreductase, a correction coefficient reflecting the amount of enzyme (enzyme activity) capable of catalyzing an oxidation reduction reaction and contributing to the electron transfer to and from the electrode, is calculated. For example, the reduction reaction current of heme is measured at a potential which is more negative than the oxidation-reduction potential of heme, to determine the variation between the sensors. This allows for clarifying the binding state of the enzyme and the electrode material, and for determining the amount of enzyme capable of catalyzing an oxidation reduction reaction and contributing to the electron transfer to and from the electrode. Thereafter, by obtaining a correction coefficient by calculating the deviation of the self-calibration result from the self-calibration curve which has been prepared in advance, and then by multiplying the measured result of glucose by the thus obtained correction coefficient, it is possible to carry out a correction for each individual sensor. The present self-calibration method can also be applied to the measurement of other substrates, by determining the oxidation-reduction potential of an enzyme by a known method. Further, the present correction method can also be applied to the evaluation of production lots during the production of the sensors. In other words, by performing a self-calibration for the sensors sampled from a production lot, an average correction coefficient of the sensors in each production lot can be calculated, which can be used as a part of a lot correction coefficient. This allows for simple correction of the measured values, without performing a self-calibration for each single measurement using a sensor.

DESCRIPTION OF SYMBOLS 1 glucose sensor
10 cover plate
11 spacer
12 base plate
13 hole
14 slit
15 capillary
16 first electrode
17 second electrode
18 reagent layer
19 insulating film
2 measuring apparatus
20 output section
21 power supply device
22 control section
23 arithmetic section
24 detection section
25 display section unit
26 battery
3 control computer
3A potentiostat
3a base plate
CR, W terminal
4 glucose sensor While the invention has been described in detail with reference to exemplary embodiments thereof, it will be apparent to one skilled in the art that various changes can be made, and equivalents employed, without departing from the scope of the invention. Each of the aforementioned documents as well as JP2016-053071 is incorporated by reference herein in its entirety.

What is claimed is:

1. A measuring method using a biosensor, the method comprising:
   introducing a sample including a substance to be measured into an electrochemical measurement cell, wherein the electrochemical measurement cell comprises:
      an insulating base plate; and
      an electrode system formed on the insulating base plate and comprising two or more electrodes, wherein at least one of the electrodes includes an oxidoreductase;
   applying a first voltage to the electrode system;
   applying a second voltage to the electrode system;
   obtaining a first signal dependent on the amount of the oxidoreductase which is capable of catalyzing an oxidation reduction reaction and contributing to an electron transfer to and from the electrode when the first voltage is applied;
   obtaining a second signal dependent on the amount of the substance to be measured in the sample when the second voltage is applied; and
   correcting the value of the second signal based on the value of the first signal, whereby to determine the concentration of the substance in the sample,
   wherein the first voltage is a voltage of not more than the reduction potential of the oxidoreductase, and the second voltage is a voltage of not less than the oxidation potential of the oxidoreductase.

2. The measuring method according to claim 1, wherein the correcting comprises:
   calculating a correction coefficient from the degree of deviation of the measured value of the first signal from a calibration curve representing the relationship between the value of the first signal and the value of the second signal; and
   determining the concentration of the substance based on the corrected value of the second signal.

3. The measuring method according to claim 1, wherein the second signal is a charge transfer limiting current.

4. The measuring method according to claim 1, wherein the oxidoreductase includes pyrroloquinoline quinone or flavin adenine dinucleotide.

5. The measuring method according to claim 1, wherein the oxidoreductase has a subunit or a domain including heme.

6. The measuring method according to claim 1, wherein the oxidoreductase has a glucose oxidation activity.

7. The measuring method according to claim 1, wherein the oxidoreductase is glucose dehydrogenase.

8. The measuring method according to claim 7, wherein the first voltage is from −0.1 to −0.2 V, and the second voltage is from 0.05 to 0.8 V.

9. The measuring method according to claim 1, wherein the electrode which contains the oxidoreductase is a direct electron transfer-type electrode.

10. The measuring method according to claim 1, wherein the sample is a biological sample.

11. The measuring method according to claim 1, wherein the substance to be measured is selected from the group consisting of glucose, cholesterol, and lactic acid.

12. The measuring method according to claim 1, wherein the sample is blood or urine.

13. A measuring apparatus comprising:
   a biosensor comprising:
      an electrochemical measurement cell comprising:
         an insulating base plate; and
         an electrode system formed on the insulating base plate, and comprising two or more electrodes, wherein at least one of the electrodes includes an oxidoreductase;
   a control section configured to control the application of a first voltage and a second voltage to the biosensor so that the first voltage is a voltage of not more than the reduction potential of the oxidoreductase, and the second voltage is a voltage of not less than the oxidation potential of the oxidoreductase;
   a detection section configured to detect a first signal and a second signal obtained by the application of the first voltage and the second voltage to the biosensor;
   an arithmetic section configured to correct the value of the second signal based on the value of the first signal, to determine the concentration of a substance in a sample; and
   an output section configured to output the calculated concentration of the substance.

14. The measuring apparatus according to claim 13, wherein the substance is glucose, and the oxidoreductase is glucose dehydrogenase.

15. The measuring apparatus according to claim 13, wherein the oxidoreductase is glucose dehydrogenase.

16. The measuring apparatus according to claim 13, wherein the substance is glucose, and the oxidoreductase is glucose dehydrogenase.

17. The measuring apparatus according to claim 13, wherein the electrode which contains the oxidoreductase is a direct electron transfer-type electrode.

* * * * *